United States Patent
Tomkins et al.

(10) Patent No.: US 11,006,655 B2
(45) Date of Patent: May 18, 2021

(54) GROWTH PERFORMANCE IMPROVEMENTS IN PASTURE AND FEEDLOT SYSTEMS

(71) Applicants: COMMONWEALTH SCIENTIFIC AND INDUSTRIAL RESEARCH ORGANISATION, Acton (AU); MEAT & LIVESTOCK AUSTRALIA LIMITED, North Sydney (AU); JAMES COOK UNIVERSITY, Townsville (AU)

(72) Inventors: Nigel William Tomkins, Camp Mountain (AU); Rocky De Nys, Townsville (AU); Robert Douglas Kinley, Acton (AU); Marie Elisabeth Magnusson, Townsville (AU); Lorenna Machado, Townsville (AU); Nicholas Andrew Paul, Townsville (AU)

(73) Assignees: JAMES COOK UNIVERSITY, Townsville (AU); COMMONWEALTH SCIENTIFIC AND INDUSTRIAL RESEARCH ORGANISATION, Acton (AU); MEAT & LIVESTOCK AUSTRALIA LIMITED, North Sydney (AU)

( * ) Notice: Subject to any disclaimer, the term of this patent is extended or adjusted under 35 U.S.C. 154(b) by 176 days.

(21) Appl. No.: 16/321,070

(22) PCT Filed: Jul. 29, 2016

(86) PCT No.: PCT/AU2016/050689
§ 371 (c)(1),
(2) Date: Jan. 28, 2019

(87) PCT Pub. No.: WO2018/018062
PCT Pub. Date: Feb. 1, 2018

(65) Prior Publication Data
US 2019/0174793 A1 Jun. 13, 2019

(51) Int. Cl.
| | |
|---|---|
| *A23K 10/30* | (2016.01) |
| *A23K 40/20* | (2016.01) |
| *A23K 50/10* | (2016.01) |
| *A23K 10/16* | (2016.01) |
| *A23K 40/10* | (2016.01) |
| *A23K 20/20* | (2016.01) |
| *A23K 20/24* | (2016.01) |
| *A61K 36/02* | (2006.01) |

(52) U.S. Cl.
CPC .............. *A23K 10/30* (2016.05); *A23K 10/16* (2016.05); *A23K 20/20* (2016.05); *A23K 20/24* (2016.05); *A23K 40/10* (2016.05); *A23K 40/20* (2016.05); *A23K 50/10* (2016.05); *A61K 36/02* (2013.01)

(58) Field of Classification Search
CPC ........ A23K 10/20; A23K 50/20; A23K 50/15; A61K 36/04
See application file for complete search history.

(56) References Cited

U.S. PATENT DOCUMENTS

| | | |
|---|---|---|
| 2002/0022049 A1 | 2/2002 | Allen et al. |
| 2011/0287132 A1 | 11/2011 | Eino et al. |

FOREIGN PATENT DOCUMENTS

| | | |
|---|---|---|
| CN | 104 026 370 | 9/2014 |
| WO | WO 2015/109362 | 7/2015 |

OTHER PUBLICATIONS

Machado et al., "The potential of macroalgae for beef production systems in Northern Australia," *J. Appl. Phycol.*, 27:2001-2005, 2015.
Machado et al., "Effects of marine and freshwater macroalgae on in vitro total gas and methane production," *PLoS One*, 9(1);e85289/1-e85289/11, 2014.
Makkar et al.,"Seaweeds for livestock diets: A review," *Animal Feed Science and Technology*, 212:1-17, 2016.
Montañez-Valdez et al., "Effect of a calcified-seaweed extract as rumen buffer on ruminal disappearance and fermentation in steers," *Indian Journal of Animal Sciences*, 82(4):430-432, 2012.
PCT International Search Report and Written Opinion issued in International Application No. PCT/AU2016/050689, dated Sep. 1, 2016.

*Primary Examiner* — Thane Underdahl
(74) *Attorney, Agent, or Firm* — Parker Highlander PLLC

(57) ABSTRACT

The invention relates to utilising red marine macroalgae to provide improvements in growth performance of livestock, particularly ruminant animals for red meat production, especially cattle, in pasture and feedlot farming systems. There is provided a method for improving the growth performance of a livestock animal in a farming system including: providing a red marine macroalgae to a farming system to enable consumption of the red marine macroalgae by a livestock animal in the farming system; thereby improving the growth performance of the livestock animal in the system.

16 Claims, No Drawings

GROWTH PERFORMANCE IMPROVEMENTS IN PASTURE AND FEEDLOT SYSTEMS

This application is a national phase application under 35 U.S.C. § 371 of International Application No. PCT/AU2016/050689, filed Jul. 29, 2016, the entirety of which is incorporated herein by reference.

FIELD OF THE INVENTION

The invention relates to improving growth performance of livestock, particularly ruminant animals for red meat production, especially cattle, in pasture and feedlot farming systems.

BACKGROUND OF THE INVENTION

One goal of a meat production system, such as beef cattle farming is to produce an animal that meets the market compliance at lowest possible cost. This requires a consideration of feed utilisation, rate of production, and quality and quantity aspects of the final product (saleable beef yield).

Depending on the relevant geography or country, livestock farming will utilise a pasture based system, a combination of pasture and feedlot and in some circumstances, ostensibly a feedlot system only.

In Australian systems, the animal is predominantly pasture farmed from birth to finishing, with some usage of feedlots depending on the productivity of the pasture and market demands. Feedlots tend to be utilised together with pasture farming in the northern Australian pastures given the lower productivity arising from grazing on native grass lands.

In Canadian systems, animals are ranch grown on pastures to become feeders, at which point they are finished in feedlots. In US systems, weaners are grown on pastures and forages, backgrounded at stocker operations on forages and then finished as feeders in feedlots.

Western European systems tend to utilise pasture farming systems to finishing, whereas Mediterranean and Central European systems utilise cropping.

Most South American systems, such as Argentina tend to utilise pasture farming although there is increasing usage of feedlots, particularly for finishing.

Generally, where economically and climactically feasible, there is a preference for pasture farming because this enables animal production at a lower cost than can be obtained by feedlot systems. Pasture farming may occur on native grasslands, or improved grasslands (introduction of legumes) or crops (for example, sugar beet, forage sorghum, failed grain crops), sometimes supplemented with other forages such as hay or silage.

One problem with pasture farming is the potentially longer time to finishing (i.e. time to obtaining the desired growth end point). This lower productivity may arise from the low metabolisable energy and protein content of the consumed plants, particularly as seen in native grassland pastures during the dry season which is an annual event across most of northern Australia.

The slower growth rates observed in pasture farming can have implications for both cost and quality of the produce. It also has implications for animal production, including time to production of animals in cycling.

Another problem with pasture farming is that it supports a lower stocking rate which limits the amount of production at any given time across an area of pasture. Further, pasture farming, particularly higher density pasture farming, requires enough pasture to enable pasture rotation so that the same pasture is not utilised immediately after it has been utilised by a prior herd. These factors all increase the costs of production in pasture farming systems.

In some pasture farming systems, forage may be supplemented with phosphorus, with urea as a non-protein nitrogen source and/or with molasses as an energy source to improve growth rate and time to finishing, or to improve the finished carcass quality. In spite of these supplements, there remains a need for alternative or improved diets for improving the outputs of pasture farming systems, particularly for improving growth rate, or reducing time to finishing.

Where pasture farming is not sufficient for finishing, the animals may be transferred to feedlots for finishing. In other farming systems, feedlots may be used for a major portion of the growing or finishing cycle, for example they may be used ostensibly for taking stored animals through to finishing commensurate with meeting market compliance for beef quality.

While feedlot systems may improve growth rate and provide positive inputs to carcass quality, they are much more expensive than pasture farming. This arises from the increased cost of feeds that generally have higher starch content, lower indigestible fibre and a higher metabolisable energy than pasture based diets.

In feedlots, diets are formulated to be a complete diet meeting animal requirements for maximum growth which is based on a least cost ration approach. To further improve cost efficiency, some diets may be supplemented with ionophores (rumensin or monensin) as rumen modifiers, in addition to phosphorus, urea and molasses. There remains a need for alternative or improved compositions for outputs of feedlot systems, particularly for improving growth rate, or time to finishing, or efficiency of feed utilisation.

SUMMARY OF THE INVENTION

The invention seeks to address one or more of the above mentioned problems or limitations and in one embodiment provides a method for improving the growth performance of a livestock animal in a pasture farming system including:

providing a red marine macroalgae to a pasture farming system to enable consumption of the red marine macroalgae by a livestock animal in the pasture farming system;

thereby improving the growth performance of the livestock animal in the farming system.

In another embodiment there is provided a method for improving the growth performance of a livestock animal in a stocker operation including:

providing an red marine macroalgae to a stocker operation to enable consumption of the red marine macroalgae by a livestock animal in the stocker operation;

thereby improving the growth performance of the livestock animal in the stocker operation.

In another embodiment there is provided a method for improving the growth performance of a livestock animal in a feedlot system including:

providing a red marine macroalgae to a feedlot system to enable consumption of the red marine macroalgae by a livestock animal in the feedlot system;

thereby improving the growth performance of the livestock animal in the feedlot system.

In another embodiment there is provided a method for increasing the growth rate of an animal in a pasture or feedlot faming system including providing a red marine macroalgae to a pasture or feedlot farming system to enable consumption of the red marine macroalgae by a livestock animal in the farming system;

thereby improving the growth rate of the livestock animal in the farming system.

In another embodiment there is provided a method for improving the efficiency of feed usage, or feed conversion ratio of a livestock animal in a farming system including:

providing a red marine macroalgae to a farming system to enable consumption of the red marine macroalgae by a livestock animal in the farming system;

thereby improving the efficiency of feed usage, or feed conversion ratio of the animal in the farming system.

In another embodiment there is provided a method for minimising the amount and/or frequency of live weight loss of a livestock animal in a farming system including:

providing a red marine macroalgae to a farming system to enable consumption of the red marine macroalgae by a livestock animal in the farming system;

thereby minimising the amount and/or frequency of live weight loss of an animal in a farming system.

In another embodiment there is provided a use of a red marine macroalgae in the manufacture of a premix, feed, feed supplement, ration or lick block for improving growth performance of a livestock animal in a farming system.

In another embodiment there is provided a use of a red marine macroalgae for improving growth performance of a livestock animal in a farming system.

DETAILED DESCRIPTION OF THE EMBODIMENTS

It will be understood that the invention disclosed and defined in this specification extends to all alternative combinations of two or more of the individual features mentioned or evident from the text or drawings. All of these different combinations constitute various alternative aspects of the invention.

The various embodiments of the invention set forth below describe the use of red marine macroalgae for providing improvements in growth performance of beef cattle in pasture farming and feedlot systems. However, it will be understood that in certain embodiments the invention is applicable to improving husbandry and growth performance of a wider range of livestock animals, especially ruminant animals including dairy cattle and ruminant animals farmed for red meat production, including sheep and goat.

In one embodiment there is provided a method for improving the growth performance of a livestock animal in a native grass land pasture farming system including:

providing an red marine macroalgae to a native grass land pasture farming system to enable consumption of the red marine macroalgae by a livestock animal in the pasture farming system;

thereby improving the growth performance of the livestock animal in the farming system.

A native grass land pasture farming system (or "unimproved pasture farming system") is generally a farming system in which animals are grazed at a low head count on indigenous grasses and forbs. Generally the pasture is extensive, covering thousands of square kilometres of land. The indigenous plants generally have a low metabolisable energy for a ruminant, being composed of plants having a high lignin content, or high insoluble starch content or other high insoluble fibre content.

In the northern farming regions of Australia, a native grass land pasture may be improved with introduced grass species such as Buffel grass, or legume species such as *Stylosanthes* spp. or leucaena (*Leucaena leucocephala*). In these regions, the animal is typically beef cattle, especially of the species *Bos indicus*, preferably of the Brahman or Brahman-related varieties, or of the species *Bos taurus*, preferably of the British or British-related varieties, or a cross of *Bos indicus* and *Bos Taurus*, known as composite breeds.

Other countries that utilise unimproved pasture farming systems include Canada and America (prairies or desert land types typical of new Mexico), Argentina and Brazil (pampas-fertile South American lowlands).

The animal may have an age from 3 to 6 months at the commencement of grazing on an unimproved pasture. At completion of grazing, the animal may be about 4 to 5 years old, and have a live weight of about 400 to 450 kg. Where the improved pasture has a higher energy provision, the live weight at finishing may be between 600 and 650 kg at about 3 to 4 years old.

The animal may receive supplementation in the form of phosphorus, urea and/or with molasses when farmed on said native grassland. The animal may also receive other forage in the form of hay, silage, legumes or lupins to manage nutritional deficits.

The macroalgae may be fresh water or marine and may be selected from the group consisting of *Asparagopsis armata, Asparagopsis taxiformis, Dictyota* spp (e.g. *Dictyota bartayresii*), *Oedogonium* spp, *Ulva* spp, and *C. patentiramea*. Preferably the algae is *Asparagopsis taxiformis*.

The algae, particularly *A. taxiformis* may be provided for consumption in a native grass land pasture farming system in an animal feed supplement as an inclusion in a mineral loose lick or lick block. As is known to those skilled in the art such loose lick or lick blocks are particularly convenient for feeding mineral supplements (as well as proteins and carbohydrates) to ruminants grazing either or both natural pastures. Such lick blocks or lick stones may comprise, in addition to the red macroalgae of the invention, various types of binders, e.g. cements, gypsum, lime, calcium phosphate, carbonate, and/or gelatin; and optionally further additives such as vitamins, trace elements, mineral salts, sensory additives, etc.

The lick block may comprises red marine macroalgae species present in an amount ranging from 0.1 to 6.0 wt %, preferably 4.0 or 5.0 wt % on a dry matter weight basis.

Preferably the lick block is formulated so as to provide the animal with about 10 to 30 g/day of red marine macroalgae species, especially of *A. taxiformis*. This amounts to inclusion rates of 1 to 3 wt % on an organic matter basis (or about 1-5% on a dry matter basis; dry matter includes organic matter and ash (minerals, calcium, etc)).

The lick block may be placed about a water station according to known and established feed supply systems, so as to encourage the animal to consume the algae incorporated in the lick block on a daily basis, or as water is required.

Generally, about the number of lick blocks required per head provide for a lick intake of about 40 to 200 g/head/day.

When animals are farmed on unimproved pastures, they tend to have fluctuations in live weight, whereby they tend to lose live weight according to environmental conditions. This ultimately impacts on the average growth rate of the animal during the period in which it is farmed on the unimproved pasture.

According to this embodiment of the invention, the animal may have an improved growth rate relative to an animal that has not consumed a red marine macroalgae such as *A. taxiformis*. In particular the average growth rate of the animal during the period in which it is farmed on the unimproved pasture may be improved by 0.1 to 0.3 kg/day compared to animal that has not consumed the red marine macroalgae. This results in an ostensible smoothing out of weight loss/weight gain and a more continuous growth pattern.

In another embodiment, there is provided a method for improving the growth performance of a livestock animal in an improved (or "cultivated") pasture farming system including:

providing an red marine macroalgae to an improved pasture farming system to enable consumption of the red marine macroalgae by a livestock animal in the pasture farming system;

thereby improving the growth performance of the livestock animal in the farming system.

An improved pasture farming system is generally a system that utilises pasture that predominantly consists of introduced species so as to be substantially devoid of indigenous plant species. The improved pasture system may essentially consist of introduced grass species.

In southern regions of Australia, examples include silver grass (*Vulpia* spp) barley grass (*Hordeum leporinum*) and capeweed (*Arctotheca calendula*), perennial rye grass (*Lolium perenne*), white clover (*Trifolium repens*), phalaris (*Phalaris aquatica*), cocksfoot (*Dactylis glomerata*), tall fescue (*Festuca arundinacea*) and subterranean clover. The cultivated pastures system may also include Lucerne (*Medicago sativa*) and legumes, lupins and the like. Cultivated pasture systems generally provide a higher metabolisable energy to the livestock animal. In these regions, the animal is typically beef cattle, especially of the species *Bos taurus* preferably of the British or British-related varieties, such as Angus or Hereford or of a European breed such as Charolais, Simmental and Limousin. Other breeds include Murray Grey, Shorthorn and Wagyu.

The animal may have an age from 3 to 6 months at the commencement of grazing on an improved pasture. At completion of grazing, the animal may be about 3 to 3.5 years old, and have a live weight of about 600 to 700 kg.

The animal may receive supplementation in the form of phosphorus, urea and/or with molasses.

The red marine macroalgae, especially *Asparagopsis taxiformis*, may be provided for consumption in a cultivated pasture farming system as an animal feed supplement in the form of a lick stone or lick block. These supplements and the composition of algae contained within them are as described above.

In other embodiments the macroalgae, especially *Asparagopsis taxiformis*, may be in the form of a feed supplement, i.e. it may be admixed with, or coated onto, forages added to the cultivated system such as hay.

The supplement may be in the form of a powder or compacted or granulated or prilled or encapsulated solid.

The supplement may comprise further ingredients and excipients that are necessary to prepare the desired product form and it may comprise further additives aimed at improving the quality of the feed and/or at improving the performance of the animal consuming the supplement. Suitable examples of such excipients include carriers or fillers, such as lactose, sucrose, mannitol, starch crystalline cellulose, sodium hydrogen carbonate, sodium chloride and the like and binders, such as gum Arabic, gum tragacanth, sodium alginate, starch, PVP and cellulose derivatives, etc. Examples of feed additives known to those skilled in the art include vitamins, amino acids and trace elements, digestibility enhancers and gut flora stabilizers and the like.

The supplement may be in the form of a compounded feed i.e. a composition which is suitable for use as an animal feed and which is blended from various natural or non-natural base or raw materials and/or additives. Hence, in particular, the term 'compounded' is used herein to distinguish the present animal feed compositions from any naturally occurring raw material. These blends or compounded feeds are formulated according to the specific requirements of the target animal. The main ingredients used in commercially prepared compounded feeds typically include wheat bran, rice bran, corn meal, cereal grains, such as barley, wheat, rye and oat, soybean meal, alfalfa meal, cottonseed meal, wheat powder and the like. A commercial compound feed will typically comprise no less than 15% of crude protein and no less than 70% digestible total nutrients, although the invention is not particularly limited in this respect. Liquid, solid as well as semi-solid compounded animal feed compositions are encompassed within the scope of the present invention, solid and semi-solid forms being particularly preferred. These compositions are typically manufactured as meal type, pellets or crumbles. In practice, livestock may typically be fed a combination of compounded feed, such as that of the present invention, and silage or hay or the like. Typically a compounded animal feed is fed in an amount within the range of 0.3-10 kg/animal/day. This may also be expressed as about 2.5 to 3.0% of live weight/day. It is within the skills of the trained professional to determine proper amounts of these components to be included in the compounded animal feed, taking into account the type of animal and the circumstances under which it is held. The compounded animal feed compositions of the invention may comprise any further feed additive typically used in the art. As is known by those skilled in the art, the term 'feed additive' in this context refers to products used in animal nutrition for purposes of improving the quality of feed and the quality of food from animal origin, or to improve the animals' performance, e.g. providing enhanced digestibility of the feed materials. Non-limiting examples include technological additives such as preservatives, antioxidants, emulsifiers, stabilising agents, acidity regulators and silage additives; sensory additives, especially flavours and colorants; (further) nutritional additives, such as vitamins, amino acids and trace elements; and (further) zootechnical additives, such as digestibility enhancers and gut flora stabilizers.

A feed premix may comprise red marine macroalgae species present in an amount ranging from 15.0 to 25.0 wt %, preferably 20.0 wt % on a dry matter weight basis.

The feed may be formulated (i.e. with supplement added to the feed) so as to provide the animal with about 10 to 30 g/day of red marine macroalgae species, especially of *A. taxiformis*. This amounts to inclusion rates of 1 to 3% (organic matter (OM) basis per day).

Animals that are farmed on improved pastures tend also to have fluctuations in live weight, although, in a comparative sense, the effect on growth rate is lesser than that observed in an unimproved pasture system. This is reflected in the higher live weight and time to finishing observed in improved pasture systems compared with unimproved systems. Nonetheless, the weight fluctuations observed in improved pasture systems do interrupt a desired continuous growth pattern that achieves a target slaughter weight.

According to this embodiment of the invention, the average growth rate of the animal during the period in which it is farmed on the improved pasture may be improved by the amounts described above in relation to farming on unimproved pastures (i.e. by 0.1 to 0.3 kg/day) compared to an animal that has not consumed the red marine macroalgae, and in some improved pastures, particularly those having a higher energy provision, the improvement in growth rate may be higher.

In another embodiment there is provided a method for improving the growth performance of a livestock animal in a stocker operation including:

providing an red marine macroalgae to a stocker operation to enable consumption of the red marine macroalgae by a livestock animal in the stocker operation;

thereby improving the growth performance of the livestock animal in the stocker operation.

A stocker operation is a farming system whereby stocker or feeder calves are placed into forage based grazing for a brief period (about 3 to 6 months) to gain weight before being placed into a feedlot. The stocker operation may utilise improved forage crops such as small grains (wheat, oats, rye, triticale) or cool season forages such as grasses and or legumes.

The animal is typically a calf of about 6 to 10 months of age and of about 200-400 kg live weight.

The red marine macroalgae, especially *Asparagopsis taxiformis*, may be provided for consumption in a cultivated pasture farming system as an animal feed supplement in the form of a lick stone or lick block. These supplements and the composition of algae contained within them are as described above.

Improved growth rates over the period in which the animal is farmed in the stocker operation may be 0.1 to 0.3 kg greater than animals that do not consume red marine macroalgae, especially *Asparagopsis taxiformis*.

In one embodiment there is provided a method for improving the growth performance of a livestock animal in a feedlot system including:

providing an red marine macroalgae to a feedlot system to enable consumption of the red marine macroalgae by a livestock animal in the feedlot system;

thereby improving the growth performance of the livestock animal in the feedlot system.

The animal is typically weaned and may have been pasture farmed on an improved or unimproved pasture before entering the feedlot.

The animal may have been farmed in a stocker operation.

The animal may have a live weight of about 320-420 kg at the time of entry to the feedlot.

At the completion of finishing in the feedlot, the animal may have a live weight of about 600 kg.

Typically the feed is provided in the form of high grain rations. The content of the ration is based on commodity prices or other economic conditions. A finishing ration may include grain at about 75%, roughage at 20%, and minerals and vitamins at about 5%. The feedlot ration may be formulated so as to provide the animal with about 10 to 30 g/day of red marine macroalgae species, especially of *A. taxiformis*. This amounts to inclusion rates of 1 to 3% (OM basis per day).

EXAMPLES

Example 1—Asparagopsis Collection

This work describes the harvesting of Asparagopsis for a feeding trial with a head of cattle which will require a minimum of 330 kg of freeze dried Asparagopsis biomass. To achieve 330 kg of freeze dried Asparagopsis biomass, 2300 kg of fresh biomass (Asparagopsis biomass reduces by approximately 85% when freeze dried) is harvested from a marine environment. The most efficient method of wild harvesting Asparagopsis is collection by hand on SCUBA. Following the harvest, biomass requires freezing as soon as possible to reduce the loss of the volatile bromoform compounds. Once frozen, the boxed and palletised Asparagopsis biomass is transported along a refrigerated logistical chain for freeze drying.

Example 2—Asparagopsis Processing

*Asparagopsis taxiformis* in the filamentous tetrasporophyte phase is collected and initially air dried on ventilated racks in the shade and then dried to constant weight in solar kilns. The dried biomass is milled to ensure a uniform product. The product is then ready for use to supply to a premix manufacturer for production of a premix.

Example 3—Formation of a Premix

A freeze or kiln dried, milled biomass formed according to Examples 1 or 2 is admixed with a commercially prepared ruminant premix including limestone, ionosphore, salt, vitamins, minerals and trace elements to form a premix having *Asparagopsis taxiformis* in an amount of 20 wt % on a dry weight basis.

Example 4—Formation of a Feedlot Ration

A premix containing the milled biomass of Example 2 is admixed with commercially prepared ruminant feedlot ration to form a feedlot ration having *Asparagopsis taxiformis* in an amount of up to 5 wt % on a dry weight basis.

Example 5—Formation of an Animal Feed

A premix containing the milled biomass of Example 2 is admixed with animal feed components including starch, fibre and protein to form an animal feed having *Asparagopsis taxiformis* at up to 5% wt % on a dry weight basis.

Example 6—Formation of a Lick Block

A dried milled biomass formed according to Example 2 is admixed with lick block components to form a lick block as follows:

| | |
|---|---|
| Molasses | 20% (w/w) |
| Urea | 5% (w/w) |
| Salt | 5% (w/w) |
| Phosphorus source | 2% (w/w) |
| Protein meal | 30% (w/w) |
| Cement | 10% (w/w) |
| Dried, milled *Asparagopsis taxiformis* | 5% (w/w) |
| Water | balance |

Provide a mould for the lick bock. Oil the inside to enable release of hardened lick block. Mix urea into molasses and then dissolve heated mixture in hot water. Then mix in salt, followed by phosphorus source, protein meal and cement. Pour into mould. Allow 7-10 days for blocks to harden.

Example 7—Utilisation of Lick Blocks and Animal Feeds in Pasture Systems

Lick blocks may be used in improved or unimproved pasture systems. In improved pasture systems, a 1 hectare pasture is stocked with about 16 animals managed as steers or heifers. The pasture will contain 1 water station and about 4 lick blocks. The lick blocks are replaced every 2 weeks.

In an unimproved pasture, animals managed as steers or heifers are stocked at 1 animal per 10 hectare. For every 10 hectares there is generally 2 water stations and 4 lick blocks. The blocks are replaced every 2 weeks.

Example 8—Utilisation of Rations in Feedlot Systems

An animal is provided for feed lot entry with a live weight of between about 320 to 400 kg. The animal is fed a feedlot ration twice per day, amounting to a total daily amount of about 10 to 12 kgs ration. This may amount to about 200 to 600 g *Asparagopsis taxiformis*/day, for at least about 70 days.

The invention claimed is:

1. A method for improving the growth performance of a livestock animal in a farming system including:
   providing a red marine macroalgae to a farming system to enable consumption of the red marine macroalgae by a livestock animal in the farming system;
   thereby improving the growth performance of the livestock animal in the system.

2. The method of claim 1 wherein the farming system is a pasture farming system.

3. The method of claim 2 wherein the pasture farming system is a native grassland pasture farming system.

4. The method of claim 2 wherein the farming system is a cultivated pasture farming system.

5. The method of claim 1 wherein the farming system is a stocker operation.

6. The method of claim 1 wherein the farming system is a feedlot system.

7. The method of claim 1 wherein the livestock animal is a ruminant.

8. The method of claim 7 wherein the animal is beef cattle, dairy cattle, sheep or goat.

9. The method of claim 1 wherein the algae is selected from the group consisting of *Asparagopsis armata, Asparagopsis taxiformis, Dictyota* spp, *Dictyota bartayresii, Oedogonium* spp, *Ulva* spp, and *C. patentiramea*.

10. The method of claim 9 wherein the macroalgae is provided in the form of a lick stone or lick block.

11. The method of claim 9 wherein the macroalgae is provided in the form of a feed for use in a pasture or feedlot system.

12. The method of claim 1 wherein the red marine macroalgae is provided to the animal at 10 to 30 g/day.

13. The method of claim 1 wherein the method improves feed conversion ratio or animal growth rate.

14. The method of claim 9, wherein the algae is selected from *Asparagposis armata* and *Asparagopsis taxiformis*.

15. The method of claim 14, wherein the Asparagopsis is provided to the animal at 10 to 30 g/day.

16. The method of claim 14 wherein the method improves feed conversion ratio or animal growth rate.

* * * * *